US00PP11708P

United States Patent [19]

Lemon

[11] Patent Number: Plant 11,708

[45] Date of Patent: Dec. 19, 2000

[54] VARIETY OF GERANIUM NAMED 'GLOBAL NEON CHERRY'

[75] Inventor: David G. Lemon, Lompoc, Calif.

[73] Assignee: Oglevee, Ltd., Connellsville, Pa.

[21] Appl. No.: 09/163,060

[22] Filed: Sep. 29, 1998

[51] Int. Cl.[7] ..... A01H 5/00

[52] U.S. Cl. ..... Plt./332

[58] Field of Search ..... Plt./332

[56] References Cited

U.S. PATENT DOCUMENTS

P.P. 9,503 4/1996 Schumann ..... Plt./332

P.P. 10,635 10/1998 Schumann et al. ..... Plt./332

*Primary Examiner*—Bruce R. Campell

*Assistant Examiner*—Wendy A. Baker

*Attorney, Agent, or Firm*—Webb Ziesenheim Logsdon Orkin & Hanson, P.C.

[57] ABSTRACT

A new and distinct ivy geranium plant with bright, hot pink blooms having burgundy veining and eyes above a medium green foliage. The new variety exhibits less oedema and is more tolerant of high heat than current market ivy geraniums.

1 Drawing Sheet

BACKGROUND OF THE INVENTION

This discovery relates to a new and distinct variety of *Pelargonium×peltatum* identified by the varietal name of 'Global Neon Cherry', Breeder No. 4DG932 and Oglevee, Ltd. No. 5210. The new variety was discovered in a selected breeding program at Oglevee, Ltd. in Connellsville, Pa. The new variety is a selection from the crossing of 'Narina' (unpatented) and the commercial variety 'Nicole', U.S. Plant Pat. No. 7,358. The new variety was first asexually reproduced on Jan. 23, 1995 in Connellsville, Pa., has been propagated by rooting tip cuttings in Connellsville, Pa. and has been found to retain its distinctive characteristics through successive generations.

The new variety, when grown in a glass greenhouse in Connellsville, Pa. using full light, 60° F. night temperature and 68° F. day temperature and grown in a soilless media with constant fertilizer at 200–250 ppm nitrogen and potassium has a response time of six weeks to flowering from a rooted cutting to flowering in a 10 cm pot.

DESCRIPTION OF THE DRAWING

The accompanying photographic drawing illustrates the new variety, with the color being as nearly true as is possible with color illustrations of this type. The colors described in the specification are seen when viewing the plant in person, and the photographic drawing illustrates the specified colors as best as possible.

DESCRIPTION OF THE NEW PLANT

The following detailed descriptions set forth the characteristics of the new variety. The data which define these characteristics were collected from asexual reproductions carried out at Oglevee, Ltd., 152 Oglevee Lane, Connellsville, Pa. 15425. The color readings on a plant in a 20 cm pot were taken indoors under 200–220 foot candles of cool white fluorescent light. Color references are primarily to the R.H.S. Colour Chart of The Royal Horticultural Society of London.

THE PLANT

Classification:

*Botanical.*—*Pelargonium×peltatum.*

*Varietal.*—Ivy leafed pelargonium named 'Global Neon Cherry'.

Height: 14.0–16.0 cm from media.

Growth: Cascading mound.

Strength: Very good outdoor performance for heat tolerance, presents a uniform cascading hanging basket.

Rooting: Cuttings produce 3 to 5 roots visible to outside of artificial growing media in 14–21 days.

Foliage: Stalked leaf attachment.

Leaves:

*Size.*—7.0–8.0 cm across.

*Shape.*—Reniform with cordate base.

*Margin.*—Pedately lobed.

*Texture.*—Leathery.

*Pubescence.*—Present.

*Color.*—Upper surface: Green Group 137A. Bottom surface: Green Group 137D. Zone: Greyed-Purple Group 183A. Leaf zones not readily apparent in the photographic illustration.

*Ribs and veins.*—Venation: Palmate. Color: Yellow-Green Group 144A.

Petioles:

*Length.*—3.0–4.5 cm.

*Color.*—Yellow-Green Group 144A.

Stem:

*Color.*—Yellow-Green Group 144A with anthocyanin staining of Greyed-Purple Group 183A.

*Internode length.*—4.0–5.5 cm.

THE BUD

Shape: Elongated.

Overall: Elliptical cluster when no color showing.

Individual buds: Elliptical or oval when no color showing.

Size: 3.0–3.5 cm when just showing color.

Number of buds per cluster: 12–21.

INFLORESCENCE

Blooming habit: Double florets; continuous flowering: 10–18 florets per umbel.

Borne: Umbel, florets on pedicel, pedicel on peduncle; 5.5–8.0 cm above foliage.

Closed florets:

*Bud size.*—1.5 cm long.

Size of fully open bloom:

*Umbel.*—5.5 cm across.

*Open florets.*—2.5–3.5 cm across.

*Form.*—Slightly cupped, ruffled.

*Color.*—Upper surface: Red-Purple Group 66A fading to Red-Purple Group 61D and to white at base. Some petals with veining of Red-Purple Group 60B. Bottom surface: Red-Purple Group 66B at edges fading to Red-Purple Group 61D and to white. Veining and eye show through the bottom side of the petals. Eye: On upper petals only, Red-Purple Group 61A. Blotch with lighter area of Red-Purple Group 62B.

*Petals.*—13–15 in number.

Texture and appearance: Smooth and satiny.

Tonality from a distance: Bright, hot pink blooms with burgundy veining and eyes above medium green foliage.

Petaloids:

*Quantity.*—1–2.

*Shape.*—Twisted, irregular.

*Color.*—Top: Red-Purple Group 66A. Bottom: Red-Purple Group 63D.

Pedicel:

*Length.*—2.5–3.0 cm.

*Color.*—Yellow-Green Group 144A with an overcasting of Greyed-Purple Group 187B.

Peduncle:

*Length.*—12.5–15.0 cm.

*Color.*—Yellow-Green Group 144A.

Disease resistance: No unusual susceptibility to diseases or pests has been noted to date.

Lasting quality: Good heat tolerance; little oedema present; continuous flowering.

REPRODUCTIVE ORGANS

Stamens:

*Anthers.*—3.0 mm long.

*Filaments.*—9–11 mm long, white in color.

*Pollen color.*—Golden orange.

Pistils:

*Number.*—1.

*Length.*—8.0–9.0 mm.

*Stigma color.*—Dark pink.

*Style.*—2.0–3.0 mm long.

*Ovaries.*—Light green in color; 5.0 mm long.

Fruit: None observed.

GENERAL CHARACTERISTICS

The new variety 'Global Neon Cherry' is a vibrant new color addition to the Global ivy series of geraniums, and to the ivy class, in general. The ease of rooting, the large cutting yield, the controlled habit and improved floret formation are similar to the other Global ivy geraniums. However, this variety exhibits less oedema and is more tolerant of high heat than current market ivy geraniums.

I claim:

1. A new and distinct variety of geranium plant named 'Global Neon Cherry' as described and illustrated herein.

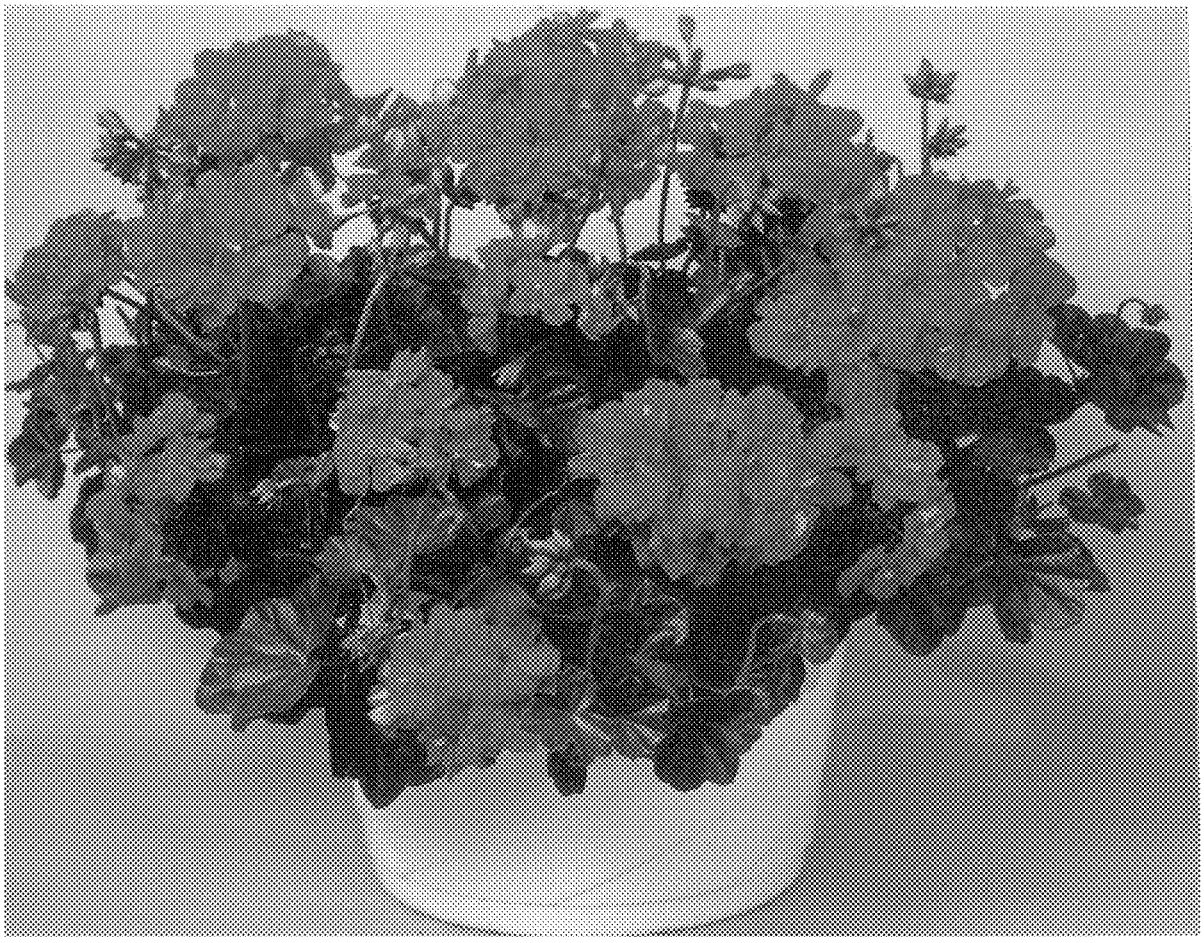

* * * * *